(12) United States Patent
Vasko et al.

(10) Patent No.: US 7,778,852 B2
(45) Date of Patent: *Aug. 17, 2010

(54) METHOD AND APPARATUS FOR MONITORING A PATIENT

(75) Inventors: Robert S. Vasko, San Diego, CA (US); Roger Massengale, Mission Viejo, CA (US)

(73) Assignee: I-Flow Corporation, Lake Forest, CA (US)

( * ) Notice: Subject to any disclaimer, the term of this patent is extended or adjusted under 35 U.S.C. 154(b) by 6 days.

This patent is subject to a terminal disclaimer.

(21) Appl. No.: 12/364,375

(22) Filed: Feb. 2, 2009

(65) Prior Publication Data

US 2009/0144093 A1    Jun. 4, 2009

Related U.S. Application Data

(60) Division of application No. 09/271,306, filed on Mar. 17, 1999, now Pat. No. 7,487,101, which is a continuation-in-part of application No. 09/141,042, filed on Aug. 27, 1998, now abandoned, which is a continuation of application No. 08/968,185, filed on Nov. 12, 1997, now abandoned.

(51) Int. Cl.
*G06F 19/00* (2006.01)
*G06Q 10/00* (2006.01)

(52) U.S. Cl. .............................................. 705/3; 705/2

(58) Field of Classification Search .................. 705/2–3
See application file for complete search history.

(56) References Cited

U.S. PATENT DOCUMENTS

| | | | |
|---|---|---|---|
| 3,872,252 A | 3/1975 | Malchman et al. | |
| 4,068,096 A | 1/1978 | Rattenborg et al. | |
| 4,207,959 A | 6/1980 | Youdin et al. | |
| 4,447,224 A | 5/1984 | DeCant, Jr. et al. | |
| 4,676,776 A | 6/1987 | Howson | |
| 4,692,147 A | 9/1987 | Duggan | |
| 4,695,954 A | 9/1987 | Rose et al. | |
| 4,731,051 A | 3/1988 | Fischell | |
| 4,782,511 A | 11/1988 | Nemec et al. | |
| 4,810,243 A | 3/1989 | Howson | |

(Continued)

FOREIGN PATENT DOCUMENTS

CA    2 291 428    6/2000

(Continued)

OTHER PUBLICATIONS

C-Phone Video Technology Selected by Strategic Monitored Services, Inc. For Home Telehealth Disease Management Application for Military Beneficiaries, Mar. 1998, Press Release Newswire.

*Primary Examiner*—Robert W Morgan
(74) *Attorney, Agent, or Firm*—Dority & Manning, P.A.

(57) ABSTRACT

A remotely programmable and accessible medical device system including an interface unit and a medical device connected to a patient is disclosed. Through a transceiver, such as a telephone or computer, a person may obtain status reports from a remotely located medical device in audible, electronic or paper form. In addition, the person may change a protocol associated with the medical device or be alerted at a remote location of an alarm associated with the medical device.

5 Claims, 15 Drawing Sheets

U.S. PATENT DOCUMENTS

| | | | |
|---|---|---|---|
| 4,838,887 A | 6/1989 | Idriss |
| 4,871,351 A | 10/1989 | Feingold |
| 4,941,172 A | 7/1990 | Winebaum et al. |
| 5,007,429 A | 4/1991 | Treatch et al. |
| 5,019,974 A | 5/1991 | Beckers |
| 5,078,683 A | 1/1992 | Sancoff et al. |
| 5,088,981 A | 2/1992 | Howson et al. |
| 5,100,380 A | 3/1992 | Epstein et al. |
| 5,119,412 A | 6/1992 | Attallah |
| 5,165,874 A | 11/1992 | Sancoff et al. |
| 5,211,626 A | 5/1993 | Frank et al. |
| 5,226,086 A | 7/1993 | Platt |
| 5,228,449 A | 7/1993 | Christ et al. |
| 5,276,611 A | 1/1994 | Ghiraldi |
| 5,311,449 A | 5/1994 | Adams |
| 5,321,619 A | 6/1994 | Matsuda et al. |
| 5,335,313 A | 8/1994 | Douglas |
| 5,338,157 A | 8/1994 | Blomquist |
| 5,369,699 A | 11/1994 | Page et al. |
| 5,375,604 A | 12/1994 | Kelly et al. |
| 5,394,445 A | 2/1995 | Ball et al. |
| 5,416,695 A | 5/1995 | Stutman et al. |
| 5,467,773 A | 11/1995 | Bergelson et al. |
| 5,474,090 A | 12/1995 | Begun et al. |
| 5,550,902 A | 8/1996 | Abbruscato |
| 5,573,506 A | 11/1996 | Vasko |
| 5,576,952 A | 11/1996 | Stutman et al. |
| 5,579,001 A | 11/1996 | Dempsey et al. |
| 5,579,378 A | 11/1996 | Arlinghaus, Jr. |
| 5,581,369 A | 12/1996 | Righter et al. |
| 5,594,786 A | 1/1997 | Chaco et al. |
| 5,626,144 A | 5/1997 | Tacklind et al. |
| 5,633,910 A | 5/1997 | Cohen |
| 5,666,404 A | 9/1997 | Ciccotelli et al. |
| 5,704,354 A | 1/1998 | Preidel et al. |
| 5,704,364 A | 1/1998 | Saltzstein et al. |
| 5,748,103 A | 5/1998 | Flach et al. |
| 5,802,494 A | 9/1998 | Kuno |
| 5,805,676 A | 9/1998 | Martino |
| 5,827,180 A | 10/1998 | Goodman |
| 5,840,020 A | 11/1998 | Heinonen et al. |
| 5,855,550 A | 1/1999 | Lai et al. |
| 5,871,465 A | 2/1999 | Vasko |
| 5,895,371 A | 4/1999 | Levitas et al. |
| 5,902,234 A | 5/1999 | Webb |
| 5,919,141 A | 7/1999 | Money et al. |
| 5,936,539 A | 8/1999 | Fuchs |
| 6,014,432 A | 1/2000 | Modney |
| 6,204,796 B1 | 3/2001 | Chan et al. |
| 6,228,057 B1 | 5/2001 | Vasko |
| 7,487,101 B1 | 2/2009 | Vasko et al. |

FOREIGN PATENT DOCUMENTS

| | | |
|---|---|---|
| WO | WO 93/14350 | 7/1993 |
| WO | WO96/16685 | 6/1996 |

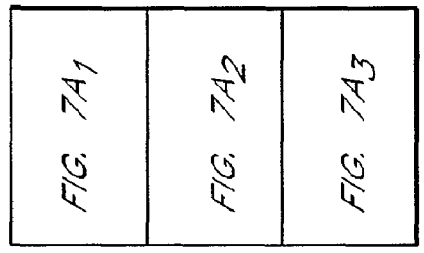
FIG. 7
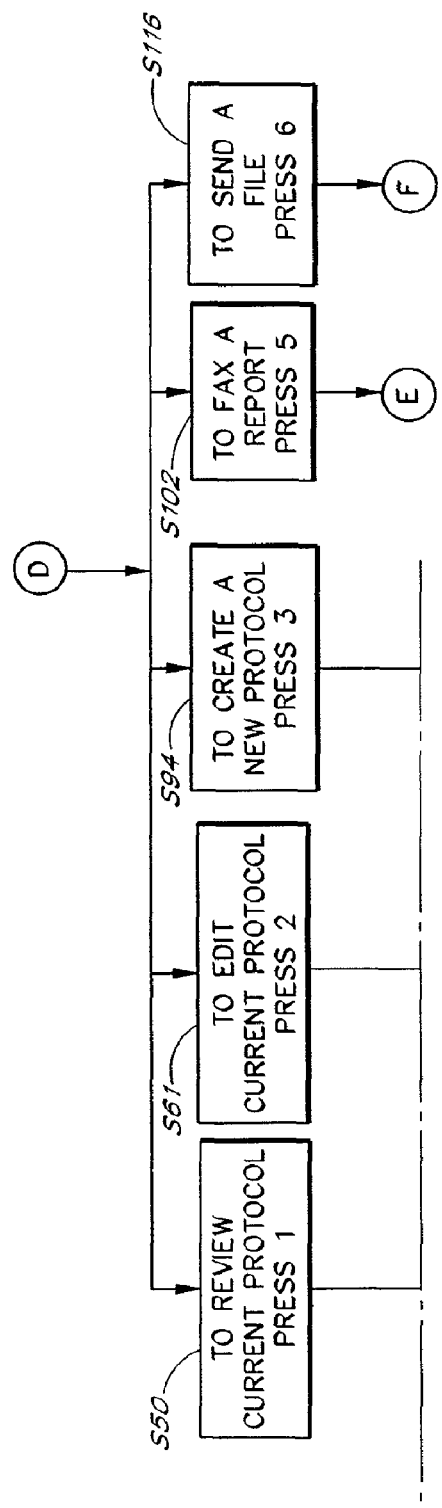
FIG. 7A₁

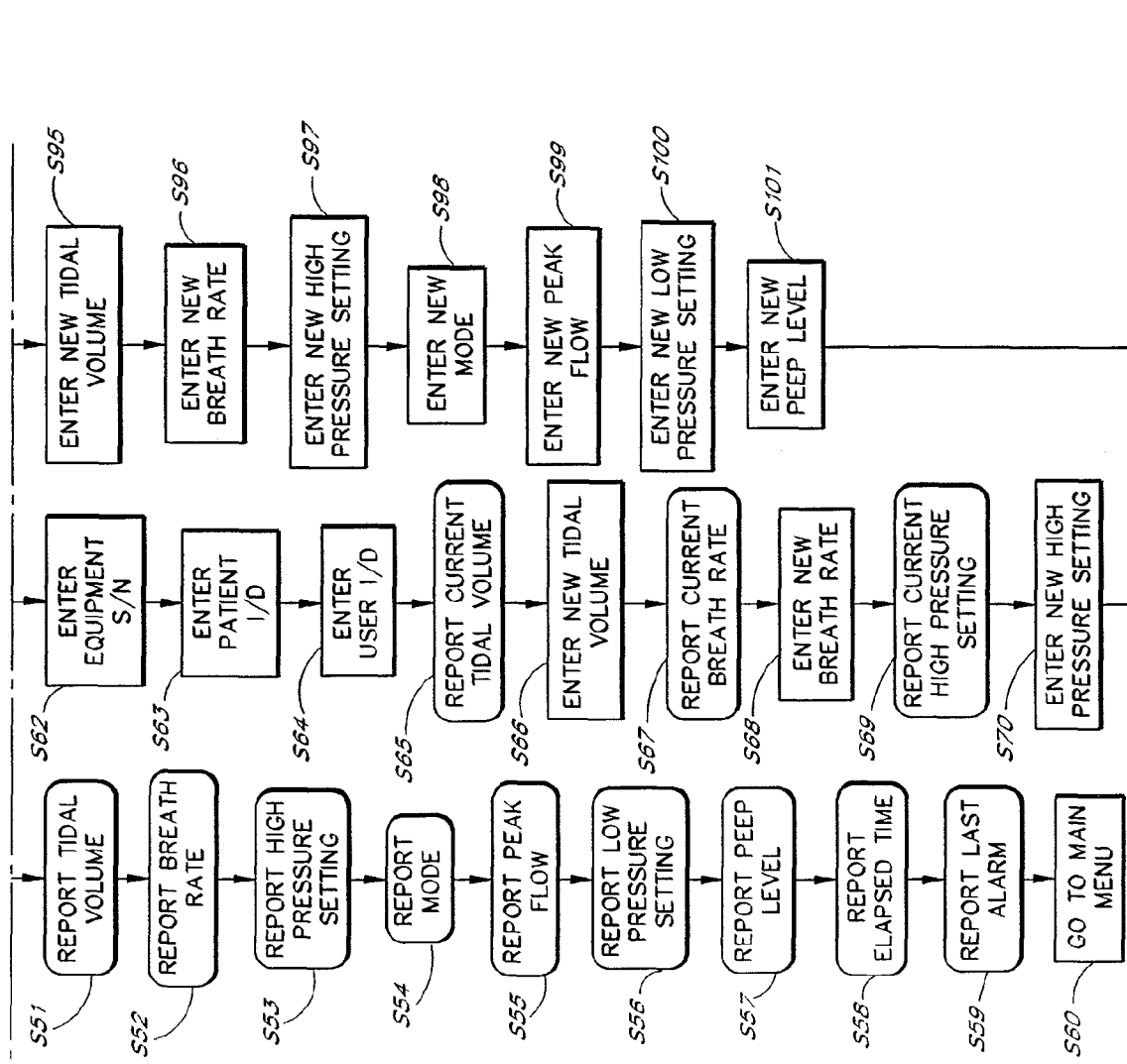
FIG. 7A₂

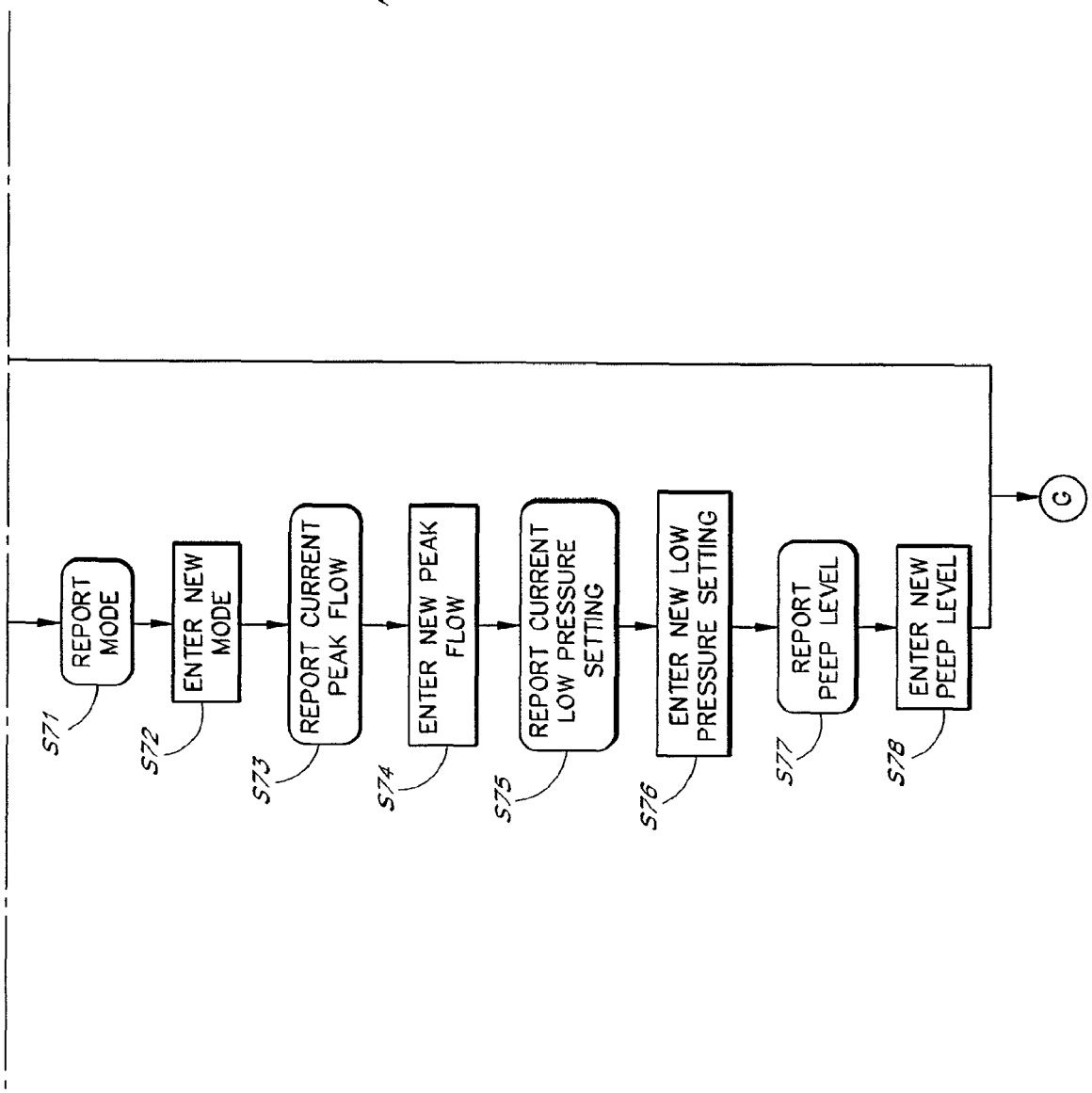
FIG. 7A₃

METHOD AND APPARATUS FOR MONITORING A PATIENT

CROSS-REFERENCE TO RELATED APPLICATIONS

This application is a divisional of application Ser. No. 09/271,306, filed Mar. 17, 1999, which will issue as Pat. No. 7,487,101, which is a continuation-in-part of application Ser. No. 09/141,042, filed Aug. 27, 1998, abandoned, which is a continuation of prior application Ser. No. 08/968,185, filed Nov. 12, 1997, abandoned.

The entireties of U.S. patent application Ser. Nos. 09/271,306, filed Mar. 17, 1999; 09/141,042, filed Aug. 27, 1998; and 08/968,185 filed Nov. 12, 1997 are hereby incorporated by reference herein and made a part of the present specification.

BACKGROUND OF THE INVENTION

Due to rising health costs, the high costs of hospital rooms, the desire to provide comfort and convenience to patients, the medical industry has promoted in-home care for patients suffering from various maladies. Many patients must be connected to various medical devices. These medical devices frequently monitor certain parameters of the patient's health and have controls which must be adjusted due to changes in the patient's needs. Therapy changes may also require that entire protocols be programmed. In early versions of these medical devices, the physical presence of a care provider was required to adjust the device's protocol. Such reprogramming is costly and time-consuming.

In addition, healthcare providers such as hospitals, and health insurance agencies paying for healthcare now often require documentation supporting all medical procedures. For example, a health insurance agency may require that a patient prove that specific parameters which measure their health are at a certain level in order for the patient to be reimbursed or the agency may require evidence that the equipment is actually being used as intended. Also, patients or their care givers at home often fail to inform the care provider that an alarm associated with a medical device has occurred and, in certain cases patients may tamper with a device in response to an alarm condition.

Therefore, a need exists for a remotely controllable medical device system that can inform care providers of a patient's status by notifying of alarm conditions and sending status reports to a remote fax or computer of the care provider or other health personnel.

Field of the Invention

The present invention relates to a remotely accessible health care system for medical applications. More particularly, the present invention relates to a system associated with a patient medical device which permits a healthcare provider located remote from the patient that permits the provider to monitor the patient's current medical condition status and with the capability of editing the patient's protocol, documents changes to the patient's protocol, and notifies the care provider of alarm conditions.

SUMMARY OF THE INVENTION

The present invention is directed to a remotely programmable medical device system and a method for remotely programming a medical device system via a remote transceiver that accomplishes the above-stated objectives.

The system of the present invention permits a care provider to obtain, from a remotely located medical device associated with a patient, the patient's status, to change the patient's protocol, or to request documentation by a remote transceiver with a touch-tone keypad after receiving voice-synthesized instructions. This method is simple to use and requires no training; it allows a care provider to perform the above functions wherever a phone is located. If the care provider has access to a computer, he has the option of performing the same functions as with the telephone, described above, but may also view the patient's real time status on the computer screen as it changes by either graphic or tabular form or send a file with the desired parameters to the system to program the medical device.

The care provider computer may also instruct the system to automatically send a status report at set time intervals to a specified location and automatically call the care provider to notify of an alarm condition. Additionally, the system may remotely program multiple medical devices connected to one or more patients or remotely program the protocol of multiple patients in a single programming session by accessing a central data storage location.

To achieve these and other advantages, and in accordance with the purpose of the invention as embodied and broadly described therein, the present invention defines a remotely programmable and accessible medical device system having a programmable protocol, the medical device system being remotely programmable by a remote transceiver, such as a touch-tone phone or computer. Alternatively, the medical device may not have a programmable protocol. For instance, the device may monitor a patient's vital signs only. The remotely programmable medical device system of the present invention comprises a memory for storing a programmable protocol or record of activity and a remote communication port for sending a voice signal to the remote transceiver, sending data to a remote fax or computer, and receiving a remote programming signal from the remote transceiver. The system also comprises a voice storage unit for storing a voice signal and a processor, coupled to: (1) the remote communication port, for processing the programmable protocol in response to receiving the remote programming signal; (2) the voice storage unit for accessing the voice signal from the voice storage unit; and (3) the memory for accessing the programmable protocol from the memory.

In an additional aspect, the present invention comprises a medical device system having a programmable alarm routine stored in a memory. The medical device system comprises a medical device which has a data port and an interface unit coupled to or integral with the medical device data port on the medical device via an interface data port. The interface unit further comprises a voice storage unit for storing a voice signal stating that an alarm condition has occurred and remote communication port for automatically sending the voice signal to the remote touch-tone transceiver or automatically sending data regarding the alarm condition to a remote fax or computer. The interface unit also comprises a processor coupled to: (1) the remote communication port, for processing the alarm condition in response to receiving the medical device alarm signals; (2) the voice storage unit for accessing the voice signal from the voice storage unit; and (3) the memory for accessing the alarm routine from the memory. A signal from the alarm on the medical device is relayed to the interface data port via the medical device data port.

In another aspect, the present invention comprises a remotely programmable medical device system having a programmable protocol stored in a protocol memory, the system being programmable by a remote transceiver. The medical device system comprises an interface unit and at least one medical device, each medical device having a data port and an interface unit coupled to or integral with each data port on the respective medical device via an interface data port. The interface unit further comprises a voice storage unit for storing a voice signal and a remote communication port for sending a voice signal to the remote touch-tone transceiver, sending data to a remote fax or computer, and for receiving a remote programming signal (such as a dual-tone multi-frequency signal in the case of a remote telephone) from the remote transceiver. The interface unit also comprises a processor, coupled to: (1) the remote communication port, for processing the programmable protocol in response to receiving the remote programming signal; (2) the voice storage unit for accessing the voice signal from the voice storage unit; and (3) the memory for accessing the programmable protocol from the memory. The processed programmable protocol is relayed from the processor to the medical device via the interface data port.

In another aspect, the present invention comprises a remotely programmable medical device system having programmable protocols for multiple patients stored in a central memory location, the system being programmable by a remote transceiver. The system comprises a remote central data storage unit, multiple medical devices connectable with multiple patients, an interface unit for each patient, and each medical device having a data port coupled to a data port on its respective interface unit. Each interface unit comprises a voice storage unit for storing a voice signal and a remote communication port for sending a digital signal to the remote central data storage location, sending data to a remote fax or computer, and for sending and receiving a remote programming signal (such as a digital signal in the case of a computer) from the remote touch-tone transceiver. Each interface unit also comprises a processor, coupled to: (1) its remote communication port, for processing the programmable protocol in response to receiving the remote programming signal; (2) its voice storage unit for accessing the voice signal from its voice storage unit; and (3) its memory for accessing the programmable protocol from its memory. The processed programmable protocol is relayed from the processor to the medical device via the interface data port. The remote central data storage unit comprises: a voice storage unit for storing a voice signal; a first communication port for sending the voice signal to the remote touch-tone transceiver, sending data to a remote fax or computer, and for receiving a remote programming signal from the remote touch-tone transceiver; and a second communication port for sending and receiving signals from the data ports of the medical devices. The remote central data storage unit further comprises a processor, coupled to: (1) the first remote communication port, for processing the programmable protocol in response to receiving the remote programming signal; (2) the second remote communication port, for processing the programmable protocol to be sent to the interface unit of a patient; (3) the voice storage unit for accessing the voice signal from the voice storage unit; and (4) the memory for accessing the programmable protocol from the memory. The processed programmable protocol is relayed from the processor of the remote central data storage unit to the processor of an interface unit via the second remote communication port.

Further objects, features, and advantages of the present invention over the prior art will become apparent from the detailed description of the drawings which follows, when considered with the attached figures.

BRIEF DESCRIPTION OF THE DRAWINGS

FIG. 7 illustrates the relationship of the diagrams in FIGS. 7A1, 7A2, and 7A3;

FIGS. 7A1-7A3 are flow diagrams illustrating a portion of a main menu of the system illustrated in FIG. 3 as adapted to use with a mechanical ventilator;

DETAILED DESCRIPTION OF THE PREFERRED EMBODIMENT

Reference will now be made in detail to the present preferred embodiment of the invention, examples of which are illustrated in the accompanying drawings. Wherever possible, the same reference numbers will be used throughout the drawings to refer to the same or like parts.

In accordance with the present invention, a remotely programmable medical device system is provided that allows remote programming and communication with a medical device from a remotely located transceiver, such as a push-button telephone or computer. The system includes a memory, a voice storage unit, a remote communication port, and a processor that is coupled to the remote communication port, the voice storage, and the memory. It should be understood herein that the terms "programming," "programmable," and "processing" are generalized terms that refer to a host of operations, functions, and data manipulation. Those terms, therefore, are not limited herein to editing and deleting data, parameters, protocol, and codes. For example, programming and processing, as used herein, may encompass editing, changing, erasing, entering, re-entering, viewing, reviewing, locking, and inserting functions.

Figure 1:
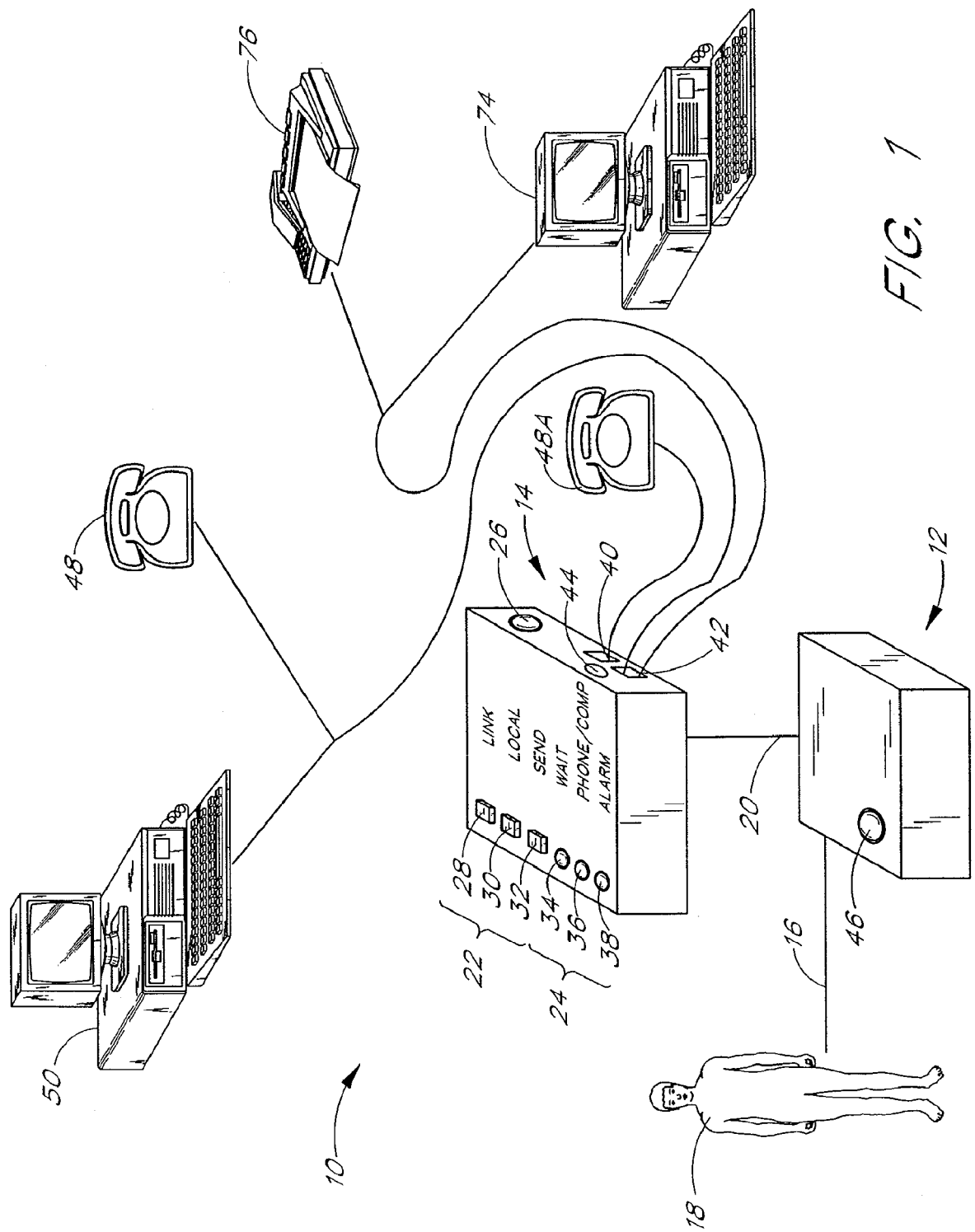
FIG. 1 schematically illustrates the medical system of the present invention by which a care provider may remotely access and control a medical device associated with a patient.

An exemplary embodiment of the system of the present invention is shown in FIG. 1 and is designated generally by reference numeral 10. As herein embodied and shown in FIG. 1, the remotely programmable medical device system 10 includes a medical device 12 and an interface unit 14. The medical device preferably includes a patient connection 16, such as a wire through which patient data is transmitted, such as from a sensor.

The interface 14 includes a cable 20 for connecting the interface 14 to the medical device 12, controls 22 for controlling operation of the interface 14, display lights 24 for indicating various conditions of the interface 14, and an internal audio device 26 for providing audio alarm signals. As embodied herein, the controls 22 include a link button 28, a local button 30, and a send button 32. Alternatively, the local button 30 may not be present as will be easily understood by those of skill in the art. The display lights 24 include a wait light 34, a phone/computer light 36, and an alarm light 38. The function of the controls 22 and the display lights 24 will be described in detail below. The interface 14 also preferably includes a remote communication port 40 and a local communication port 42.

In the alternative to being coupled via wiring 20, the interface 14 and medical device 12 may communicate via an interface data port 44 and a medical device data port 46 each comprising a wireless emitter/detector pair. Preferably, data ports 44, 46 each comprise an infra-red or RF emitter/detector, permitting wireless communication between the medical device 12 and the interface 14. Other wireless communications ports may also be used. A power cable 20 is preferably employed to provide power to the medical device 12 via the interface 14. Alternatively, the medical device may have its own power cable coupled directly to the power source (not shown), as opposed to being connected through the interface 14.

As embodied herein, the remote communication port 42 and the local communication port 40 (if present) each comprise a standard modem, as is well known in the art. The modem may operate at 28800 baud or other baud rates. The system may be arranged so that a care provider located close to the patient, such as at a patient station in a hospital when the patient is in the hospital, can access the interface 14 through the local port 40, such as through a hard wire link. On the other hand, if the care provider is at a location remote from the medical device system 10, the system is preferably arranged so that when the link button 28 is pressed, the remote communication port 42 is activated. In this way, the care provider can communicate with the interface 14 via a remote transceiver such as a telephone 48 or a computer 50. It should be understood that the interface 14 may be provided with but a single port through which signals are input and output, instead of having separate local and remote ports.

For convenience, this description refers to a care provider's use of a telephone or personal computer to access the medical device 12 remotely, but it should be understood that any transceiver capable of activation or selection of programming parameters both independently of and in response to various prompts and queries. It should also be understood that the term "remote touch-tone transceiver" is not limited to conventional push-button telephones having a 12 key keypad, with 0-9, *, and # keys. Rather, as defined herein, the term "touch-tone transceiver" refers to any transceiver capable of generating signals via a keyboard or other data entry system and thus is not limited to transceivers that generate DTMF signals, such as conventional telephones. Examples of other types of "touch-tone transceivers" as defined herein include computers having a keyboard and/or cursor-controlling device, conventional push-button telephones, transmitters that convert human voice to pulse or digital or analog signals, and pager transceivers.

Figure 2:
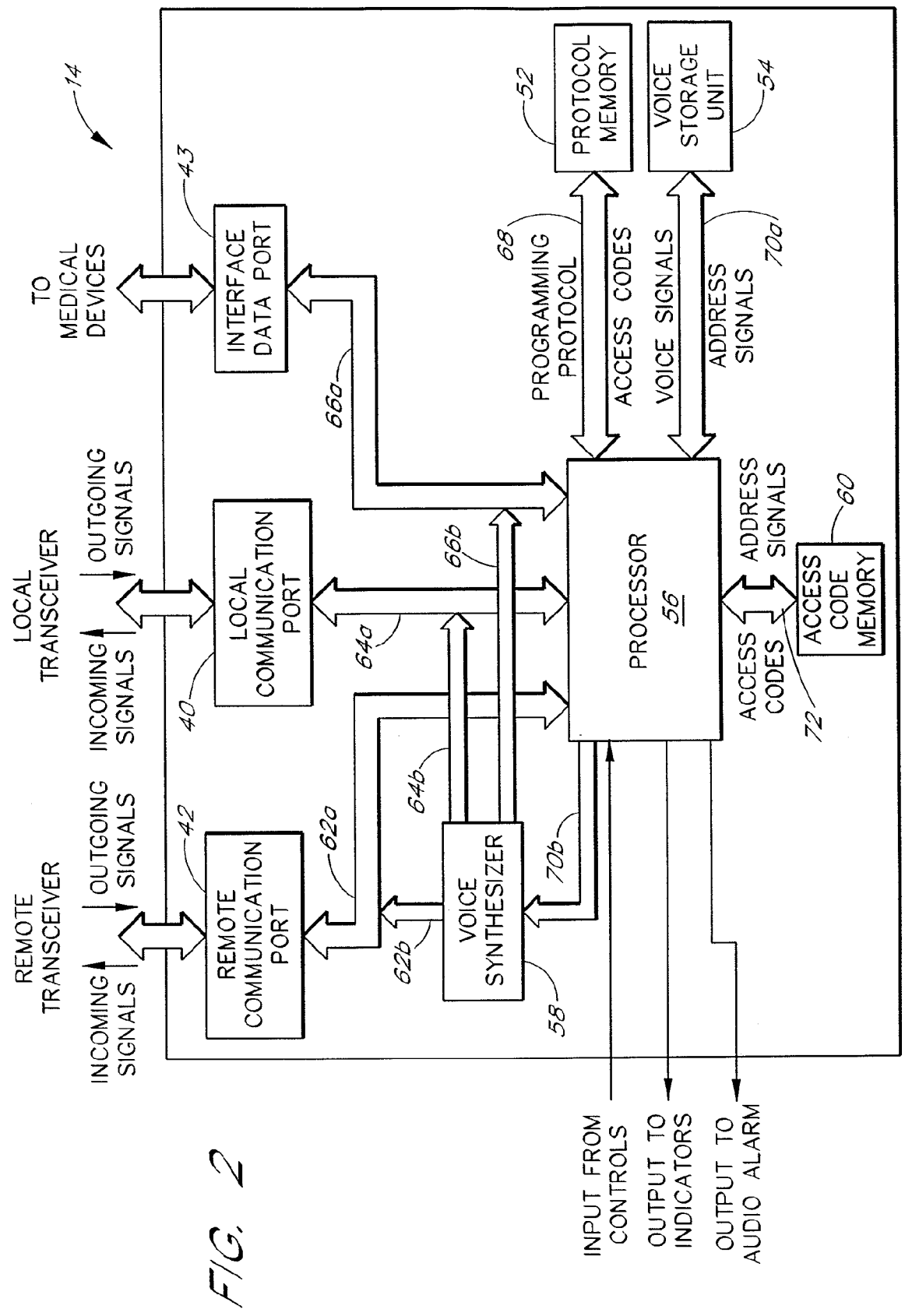
FIG. 2 schematically illustrates an interface arrangement of the system illustrated in FIG. 1.

With reference to FIG. 2, the elements included in the interface 14 will be described in more detail. As stated above, the interface 14 comprises the remote communication port 42, the local communication port 40, a protocol and event memory 52, a voice storage unit 54, a processor 56, a voice synthesizer 58, and an access code memory 60. Alternatively, the protocol and event memory 52 and the processor 56 may be an integral unit. The protocol memory 52, the voice storage unit 54, and the access code memory 60 may all be contained in the same memory device (such as a random access memory), or in separate memory units. Preferably, the voice storage unit 54 comprises a read-only memory (ROM). The interface 14 also includes the data port 43 for relaying information between the interface 14 and the medical device 12 (such as through wire 20 or by the emitter/detector 44). The voice synthesizer 58 is preferably an integrated circuit that converts digitized voice signals to a signal that emulates the sound of a human voice. As embodied herein, the voice synthesizer 58 needs only be used to convert the signals outgoing from the interface 14 to the remote telephone 48 and thus is not required for converting incoming signals from the remote telephone 48 or from the remote computer 50 or outgoing signals to a remote computer 50. The voice synthesizer may comprise a commercially available speech synthesis chip.

The remote communication port 42, the local communication port 40, and the interface data port 44 are all coupled to the processor via data buses 62a, 64a, and 66a, respectively. The communication ports 40, 42 receive signals from the transceiver 48, 50 and relay those signals over the buses 62a, 64a, respectively to the processor 56 which in turn processes those signals, performing various operations in response to those signals. If the care provider chooses the remote communications mode from the telephone 48, the processor 56 receives digitized voice signals from the voice storage unit 54 via bus 70a and sends those digitized voice signals to the voice synthesizer 58 via bus 70b, where the signals are converted to human voice emulating signals. Those human voice signals are sent from the voice synthesizer 58 via buses 62b, 64b, 66b to buses 62a, 64a, 66b, which in turn relay those signals to the remote communication port 42, the local communication port 40, and the interface data port 44, respectively.

For example, if it is necessary provide instructions to the care provider operating the remote telephone 48. The processor 56 sends a voice address signal over a data bus 70a coupling the processor 56 to the voice storage unit 54. The voice address signal corresponds to a location in the voice storage unit 54 containing a particular voice signal that is to be sent to the remote transceiver 48. Upon receiving the voice address signal, the particular voice signal is accessed from the voice storage unit 54 and sent, via the data bus 70a, to the processor 56. The processor 56 then relays the voice signal via the data bus 70b to the voice synthesizer 58, which converts the voice signal and sends the converted signal via data buses 62b and 62a to the remote communication port 42, which sends the converted signal to the remote transceiver 48.

The voice signal retrieved from the voice storage unit 54 may be a digitized representation of a person's voice or a computer generated voice signal (both being well known in the art). The digitized voice signal is converted by the voice synthesizer 58 to a signal that emulates the sound of a human voice. The voice signal instructs the care provider on how to respond to the voice signal and what type of information the care provider should send. As the remote transceiver may be a push-button telephone having a keypad with multiple keys, the care provider then presses the appropriate key or keys, thereby sending a DTMF signal back to the remote communication port 42 of the interface 14. It should be understood, however, that the remote transceiver need not be a push-button telephone, but rather any transceiver capable of sending and receiving DTMF or other similar signals. For example, the remote transceiver may be a computer or portable remote controller.

If the DTMF signal sent by the care provider is a remote programming signal which is transmitted from the remote telephone 48 to the remote communication port 42 of the interface 14, the remote communication port 42 then relays the remote programming signal via the data bus 62*a* to the processor 56. In response to receiving the remote programming signal, the processor 56 accesses a particular parameter of the programming protocol from the protocol memory 52. To access the parameter, the processor 56 transmits a protocol address signal over the data bus 68 that couples the processor 56 and the protocol memory 52. The protocol address signal corresponds to a location in the protocol memory 52 containing the parameter. The. parameter is then sent from the protocol memory 52 to the processor 56 over the data bus 68. Depending on the nature of the remote programming signal, the processor 56 can then perform one of a number of operations on the parameter, including editing, erasing, or sending the parameter back to the remote transceiver 48, 50 for review. Those skilled in the art will recognize that many types of signals or commands can be sent from the remote transceiver 48, 050 to the interface 14 for processing. Examples of such signals, how they are processed, and their effect will be described in detail below in conjunction with the description of the operation of the present invention.

In accordance with the present invention, the medical device system 10 can incorporate various security measures to protect against unwanted access to the interface 14 and the associated medical device 12. Significantly, a user access code can be used to block access except by persons with the user access code, which may be a multi-digit number (preferable a four digit number.) The medical device system 10 can be equipped with one or multiple user access codes, which are stored in the access code memory. To initiate communication with the medical device system 10, a care provider is connected to the medical device system 10 via the remote touch-tone transceiver 4 50. This connection may be initiated by a call from the care provider to the medical device system 10 (or a patient talking on a telephone located near the medical device system 10), or by a call from the patient to the care provider, Either way the care provider is connected to the medical device system 10. After the connection is made between the care provider and the medical device system 10, the interface 14 is preferably arranged to require care provider to enter a user access code. If the care provider enters a valid user access code (as explained above, there may be several valid codes), the care provider is permitted to access and/or program the programmable protocol.

During a programming session, in certain circumstances (which will be described below), the user access codes can be reviewed, edited, and/or erased entirely and re-entered. To perform any of these functions, a programming signal is sent by the care provider from the remote transceiver 48, 50 to the interface 14. That programming signal is relayed through the remote communication port 42 to the processor 56, which processes the signal and generates an access code address signal. The access code address signal, which corresponds to a memory location in access code memory 60 holding a user access code, is sent over a data bus 72 to the access code memory 60. The particular user access code is then retrieved and sent back of the data bus 72 to the processor 56, which processes the user access code in some manner.

To communicate with the medical device system 10, the interface is equipped with the interface data port 43. The medical device protocol can be sent from the interface 14 to the medical device 12 via the interface data port 43 and the medical device data port 46. Thus, for example, the processor 56 accesses the protocol from the protocol memory 52 and sends the protocol via data bus 66*a* to the interface data port 43. The interface data port 43 then sends the information to the medical device data port (such as through the wire 20 or the wireless emitter/transceiver 46), where it is processed by circuitry and/or software in the medical device 12. In this way, the medical device protocol can be programmed (e.g., edited, redone, reviewed, locked, re-entered, etc.).

The send button 32 is designed to permit sending of the medical device data or protocol to a remote location, such as a computer 74 or fax machine 76. In this way, a remote record is maintained, such as at a computer. If the computer 74 is remote from the medical device system 10, a person located at the interface 14 may press the send button 32, which in turn downloads the existing protocol or data to the remote communication port 42. The protocol is then transmitted via the remote communication port 42 to the remote computer 74.

The link button 28 is preferably used to initiate or enter into the remote programming mode of the medical device system 10. When initiating a programming session, the care provider calls the telephone number corresponding to the medical device system 10 (or the patient's home phone). The patient 18 may answer the call with his or her telephone, and the care provider and patient can communicate by standard voice signals. This is known herein as a phone mode or patient conversation mode. The care provider then instructs the patient to depress the link button 28, which disconnects the patient 18 from the telephone line and initiates the programming mode described below with reference to FIGS. 3-8. If, however, the patient 18 does not answer the care provider's call, the interface 14 may be equipped with an internal switching system that directly connects the care provider with the interface 14 and initiates the programming mode. The internal switching may be accomplished with hardware in the interface 14 or with software that controls the processor 56, or with a hardware-software combination. Either way, the care provider may then begin processing the information and protocol stored in the interface 14. (As described above, the call may be initiated by the patient 18 to the care provider.)

The functions of the display lights 24 will now be described. Preferably, the display lights 24 comprise LED's. The wait light 34 indicates when the interface 14 is involved in a programming session or when it is downloading the protocol to a remote location, such as the remote computer 74. Accordingly, the wait light 34 tells the patient 18 not to disturb the interface 14 until the wait light 34 goes off, indicating that internal processing elements of the interface 14 are inactive. The phone light 36 indicates when the care provider and the patient 18 are involved in communication via the remote transceiver 48 or 50 and thus when the internal processing elements of the interface 14 are inactive. The phone light 36 may also indicate when the medical device system 10 is ready.

The alarm light indicates various alarm conditions and functions of the medical device system 10. The medical device 12 sends an alarm signal via the medical device data port to the interface data port 43. The signal is relayed via data bus 66*a* to the processor 56. Next, the processor 56 sends a voice address signal over data bus 70*a* coupling the processor 56 to the voice storage unit 54. The voice address signal corresponds to a location in the voice storage unit 54 containing a voice signal pertaining to the alarm condition that is to be sent to a remote location (such as 48, 50, 74, or 76). Upon receiving the alarm address signal, the alarm signal is accessed from the voice storage unit 54 and sent via the data bus 70a to the processor. The processor 56 then relays the voice signal via the data bus 70b to the voice synthesizer 58 which converts the voice signal and sends the converted signal via data buses 62a, 62b to the remote communication port 42 which sends the converted signal to the remote transceiver.

Remote Access of a Medical Device with the System of the Present Invention

Figure 3:
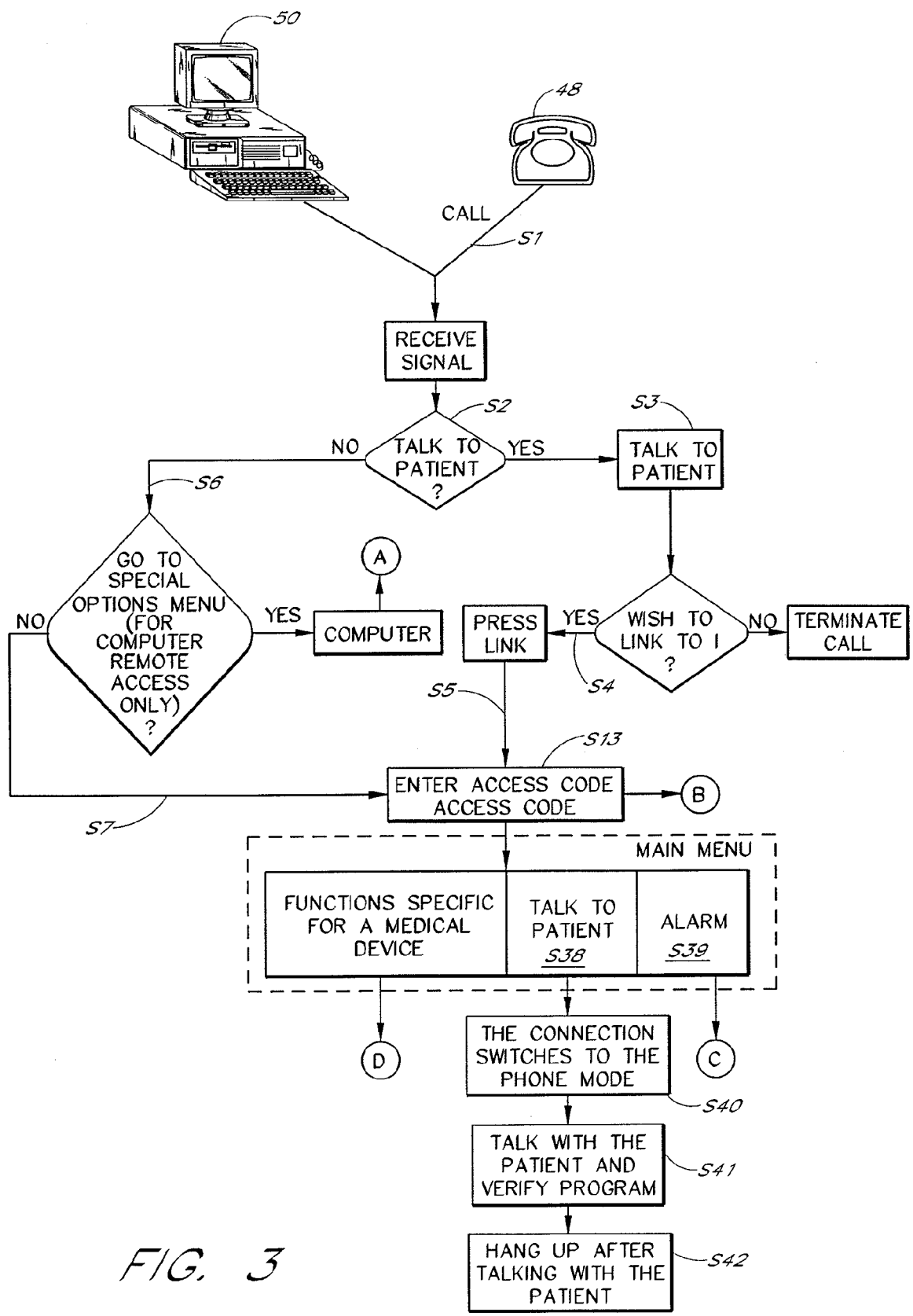
FIG. 3 is a flow diagram illustrating a general control methodology of the interface.

Referring to FIG. 3, the programming mode or sequence of the present invention will be described in detail. A care provider may access and process the protocol of the interface from either the remote telephone 48, remote computer 50 or other transceiver, as described above. The programming mode by remote telephone 48 will first be described. The care provider dials the telephone number corresponding to the medical device (Step 1). A synthesized voice message will ask the care provider whether the care provider wishes to first converse with the patient prior to the remote programming session (Step 2). If the care provider chooses "yes," the care provider and patient communicate by standard voice signals (Step 3). More specifically, the patient would pick up local phone 48A which is in communication with the local port 40 and speak with the care provider who is on the remote phone 48 in communication with the remote port 42. (See FIG. 1.) After the conversation is completed, the care provider asks the patient to depress the link button on the interface (Step 4), which connects the care provider with the interface (Step 5), terminates the phone mode, and initiates a remote touch-tone programming session. If the care provider chooses not to talk to the patient before the remote programming session (Step 6), the care provider may choose "no" (Step 6), and is directly connected to the interface 14, thereby directly initiating a remote touch-tone programming session by going to the access code menu (FIG. 5) without entering into conversation mode.

Figure 4:
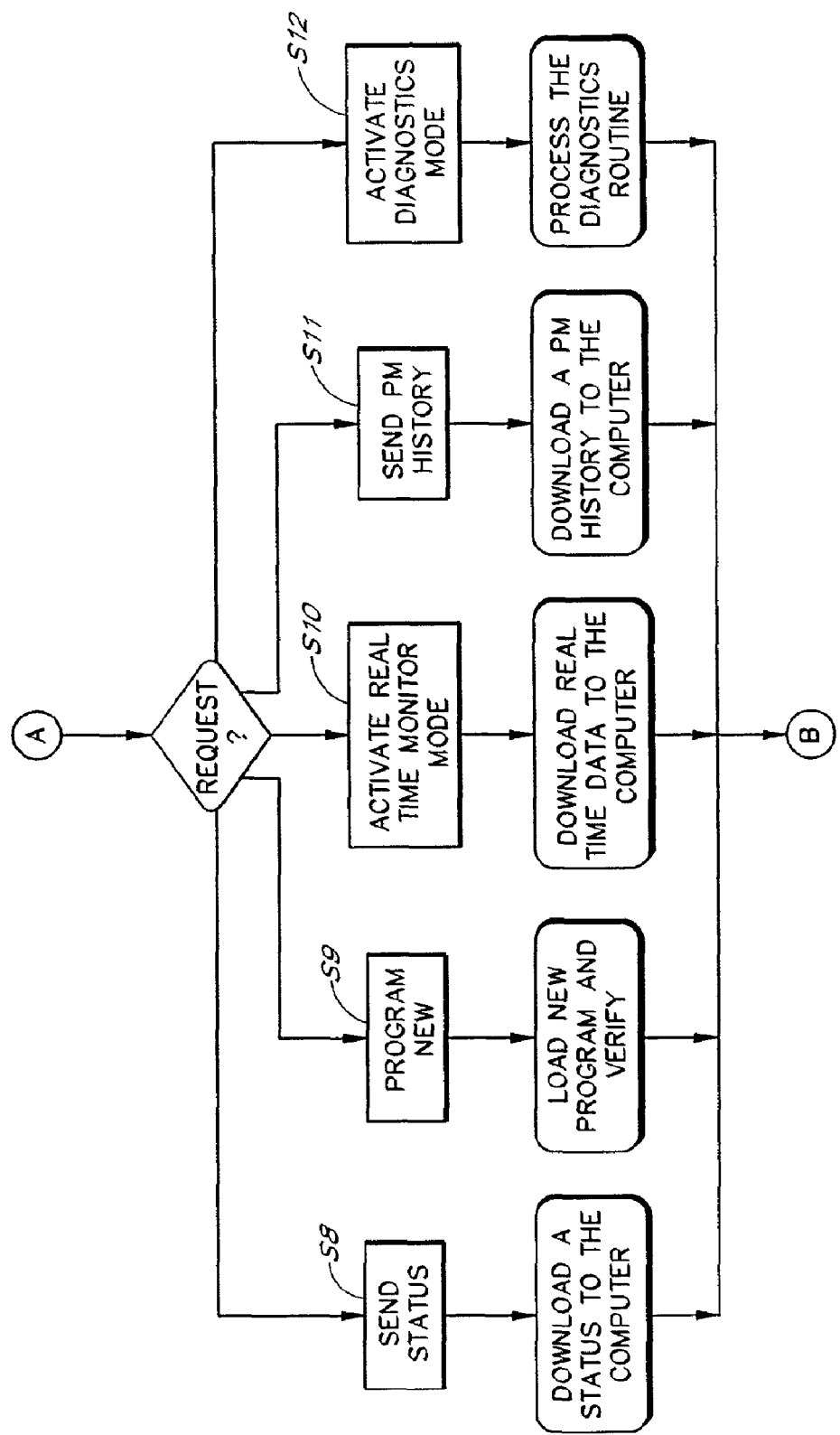
FIG. 4 is a flow diagram illustrating a computer programming mode of the system.
Figure 5:
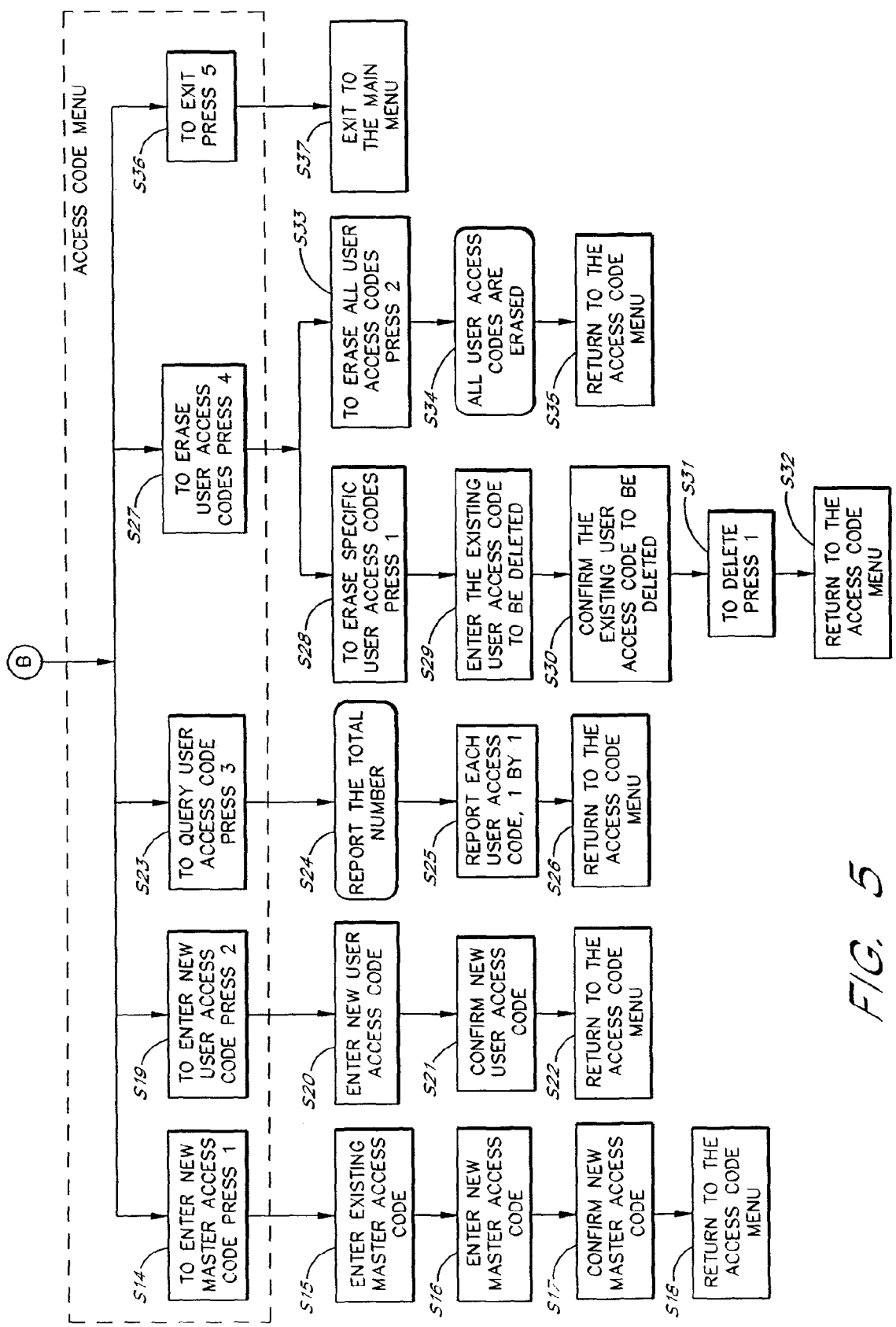
FIG. 5 is a flow diagram illustrating an access code menu of the system.

Alternatively, the care provider may access and process the protocol of the interface from a remote computer 50. The care provider may directly initiate programming mode by having the modem of the remote computer 50 dial the number of the medical device system 10. In the event that the device 10 is only monitoring a patients vital signs, the care provider can retrieve the vital signs as will be understood by one of skill in the art. Initially, a message will appear on the care provider's computer screen querying the care provider whether the care provider wishes to view a menu with additional options before going to the main menu. As shown in FIG. 4, such options include, but are not limited to: sending the status of the patient's condition to the care provider's computer (Step 8); loading a new protocol from a file on the provider's computer (Step 9); activating real time monitor mode so that the provider may view the patient's current condition as it changes (Step 10); receiving the PM history of the device (Step 11); and activating the diagnostics mode (Step 12). If the care provider chooses not to go to the special options menu (Step 7), he may go directly to a remote programming session by going to the access code menu (FIG. 5).

Access Code

If the user enters a correct access code (Step 13), the user is preferably allowed to perform certain functions relating to the access code. For example, and referring to FIG. 5, if the care provider has entered a master access code, the interface 14 generates a number of voice queries (for a telephone link; a signal representing alphanumeric text of the same message may be transmitted when a computer 50 is being used), that are transmitted to the care provider and provide the care provider with a number of options. First, in Step 14, the care provider is asked whether a new master access code is to be entered and is instructed to press a certain button on the touch tone keypad (in this case the number "1") to select this option. If the care provider selects this option, the interface 14 tells the care provider to enter the existing master access code (Step 15) and to enter a new master access code (Step 16). The newly entered master access code is then read back to the care provider by the interface 14 (Step 17), and the interface 14 generates a voice command that tells the care provider to press the "#" key on the keypad to accept this new master access code). If the care provider presses the "#" key, the interface 14 returns (Step 18) the care provider to the access code menu. Those skilled in the are will recognize that the keys to be pressed by the care provider are only exemplary and that other keys could be designated to accept and/or select various options and programming entries.

Second, in Step 19, the care provider is asked whether a new user access code is to be entered and is instructed to press a certain button on the touch tone keypad (in this case the number "2") to select this option. If the care provider selects this option, the interface 14 tells the care provider to enter a new user access code (Step 20). If the entered new user access code already exists, the program loops around and asks the care provider to enter a new master access code again (not shown). If the newly entered user access code does not already exist, the new user access code is then read back to the care provider by the interface 14 (Step 21), and the interface 14 generates a voice command that tells the care provider to press the "#" key on the keypad to accept this new user access code. If the care provider presses the "#" key, the interface 14 returns (Step 22) the care provider to the access code menu.

Third, in Step 23, the care provider is asked whether he or she would like to query the user access codes and is instructed to press a certain button on the touch tone keypad (in this case the number "3") to select this option. If the care provider selects this option, the interface 14 tells the care provider in Step 24 that there are a certain number of user access codes (depending on how many there are). In Step 25, the interface 14 recites the user access codes to the care provider and continues reciting the user access codes until all are recited. After completing reciting the user access codes, the interface 14 returns (Step 26) the care provider to the access code menu.

Fourth, in Step 27, the care provider is asked whether he or she would like to erase the user access codes and is instructed to press a certain button on the touch tone keypad (in this case the number "4") to select this option. If the care provider selects this option, the interface 14 asks the care provider to select one of two options: (1) to erase specific user codes, press a certain button on the touch-tone keypad (in this case the number "1") (see Step 28); or (2) to erase all user access codes, press a different button (in this case the number "2") (see Step 33). If the care provider selects Step 28, the care provider is asked to enter the specific user access code to be deleted (Step 29), and the interface 14 reads back that specific user access code in Step 30. The interface 14 then asks the care provider to press the "#" button on the touch-tone keypad to accept deletion of that user access code and is returned to the access code menu. If the care provider selects Step 33 (global deletion), the interface 14 warns the care provider that he or she is about to erase all the user access codes and asks for the care provider to press the "#" button to accept (Step 34). The interface then returns (Step 35) to the access code menu.

Fifth, in Step 36, the care provider is asked to press a certain number (in this case "5") to exit the access code menu. If the care provider selects this option, the interface 14 returns (via Step 37) to the access code prompt.

The interface 14 may also be programmed so that access is prevented without entry of an access or security code (not shown).

Main Menu

If the care provider has entered a correct user access code and has either by-passed the above functions relating to the access code or has completed them, the processor 56 accesses from the voice storage unit 54 (or by a signal representing alphanumeric characters transmitted to a computer) a number of voice queries comprising a main menu. Referring to FIG. 3, a number of options are presented to the care provider through the main menu. The particular items presented may vary depending upon the particular medical device with which the system is being used, the number of medical devices being used with the system (as described below), or the number of patients that are connected to the system (as described below).

The main menu of FIG. 3 illustrates a menu which is generally useful with a wide range of medical devices and which presents a number of advantageous procedures of the system of the present invention. It should be understood that other menu features may be provided. As illustrated, the care provider is asked to select among several options by pressing a key on the touch-tone keypad (or on a computer keypad).

Figure 6:
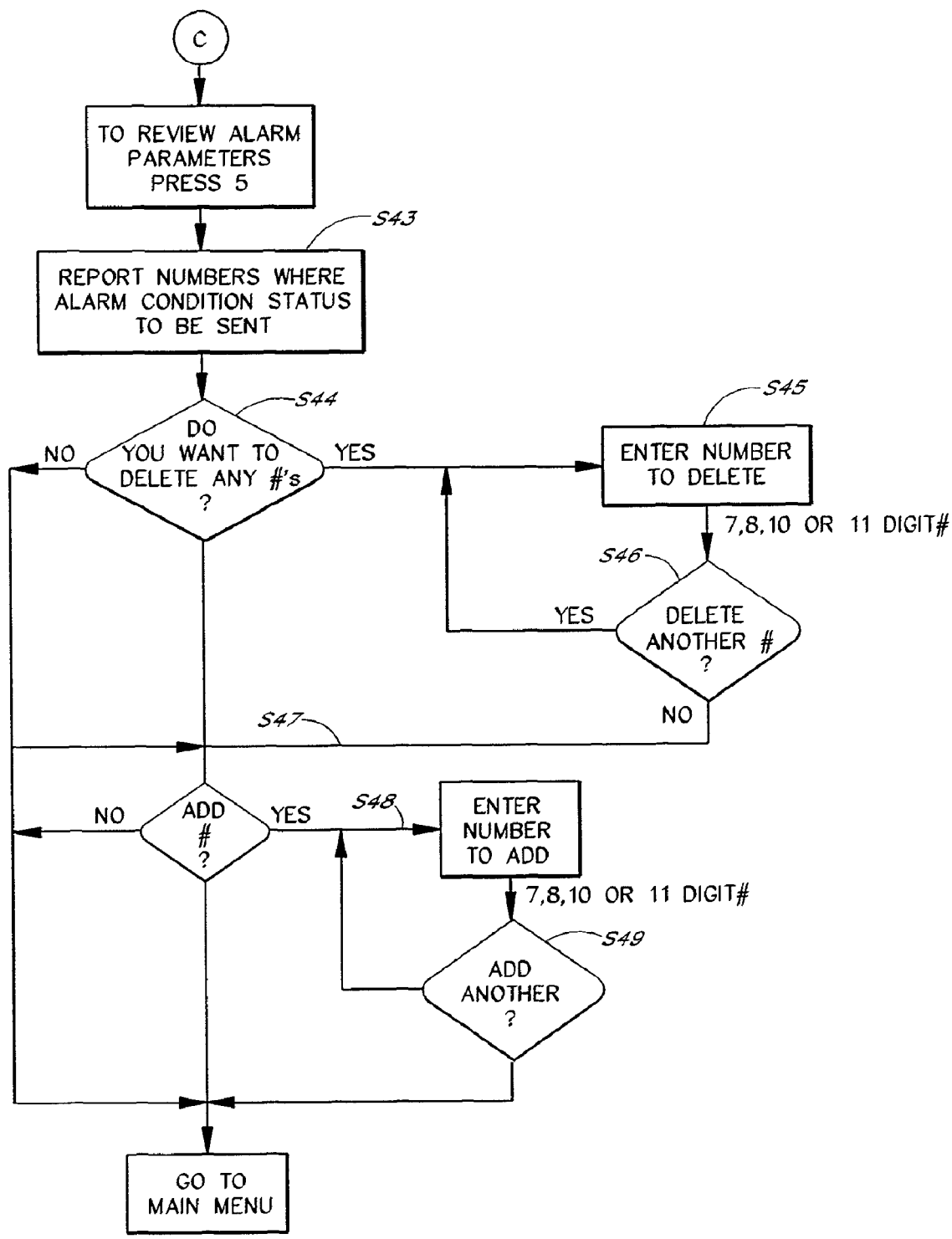
FIG. 6 is a flow diagram illustrating an alarm control menu of the system.

Certain options will be applicable for every medical device such as talking to the patient (Step 38) and the alarm review mode (Step 39). If the care provider selects direct conversation with the patient, the connection is switched to a phone mode (Step 40). In the phone mode, the care provider can talk with the patient to verify programming changes (Step 41). The care provider can then hang up the remote telephone 48 after completing conversation with the patient (Step 42). If the care provider selects the alarm review mode in Step 39, the interface generates voice queries that are transmitted to the care provider. As illustrated in FIG. 6, the care provider has the option of reviewing the fax or phone number(s) that will be automatically dialed in the case of an alarm condition. For example, the synthesized voice will state, "alarm notification number one is 123456790; alarm notification number two is 2345678" (Step 43). In Step 44, the care provider has the option of deleting an existing number by entering in the number to be deleted through the transceiver (Step 45). The care provider may choose to delete additional numbers (Step 46), or go to the add alarm notification option (Step 47). If the care provider selects the option of adding additional alarm notification numbers in Step 48, the care provider may add an additional number by entering in the number to be added through the transceiver. In Step 49, the care provider is asked to either add another number or go to the main menu.

Options such as faxing a report or sending a file are also applicable for every medical device, but the type of report or file will vary depending on the medical device. Other options may be applicable to some medical devices, such as editing or creating a protocol, but not others. Therefore, these non-universal options are discussed below (refer to step or circle "D") as related to specific medical devices.

Adaption of the System of the Present Invention to Multiple Medical Devices and/or Multiple Patients In a variation of the present invention, the system may be arranged to permit access to and control over multiple medical devices. In this arrangement, multiple medical devices are preferably arranged to communicate with a single interface. In a method of accessing and controlling these multiple devices, after entering the access code, the care provider will be prompted to enter the device number of the particular device which the care provider wants to access.

Another embodiment functions in the same manner as the embodiment described above. However, this embodiment may be used for multiple patients and comprises multiple medical devices connectable with multiple patients, an interface unit coupled with the medical devices of each patient, and a central data storage unit. The central data storage unit performs the same function as an interface unit, but acts as a central storage location for the protocols of multiple patients. This embodiment allows the care provider the option of calling one number from the remote transceiver, the number of the central data storage unit, to program the protocols of multiple patients instead of calling the number of each patient; however, the care provider still retains the option of calling the interface unit of a particular patient if the care provider wishes to program the protocol of a single patient. The remote central data storage unit comprises two remote communication ports, a protocol and event memory, a voice storage unit, a processor, a voice synthesizer, and an access code memory. The protocol memory, the voice storage unit, the voice synthesizer, and the access code memory are the same as those for the interface units. Each of the two remote communication ports is coupled to the processor via data buses. The first remote communication port receives signals from a remote transceiver and relays those signals over the buses to the processor which performs various operations in response to those signals. Next, the signals are sent by a data bus to the second remote communication port which then relays the signals to the specified interface unit via the remote communication port of the interface unit. The signals are then processed in the same manner as the interface unit processor without a central data storage unit processes the signals it receives from the remote touch-tone transceiver.

It should be understood that the above programming and functions described above provide only examples of how the care provider, interface unit, and central data storage unit may interact via a remote touch-tone transceiver. Therefore, additional or alternative steps and procedures can be designed and implemented for remote programming of the present invention. Accordingly, only some of the steps described above need be included in the invention; the steps may be conducted in a different order; additional or fewer protocol parameters may be controlled by the care provider; and different operational modes may be chosen.

Furthermore, the present invention can be used with a variety of medical devices. As discussed below, the present invention is used for reviewing and programming the protocol of a mechanical ventilator and a vital signs monitor. It will be apparent to those skilled in the art that various modifications and variations can be made in the apparatus and method of the present invention without departing from the spirit or scope of the invention. Thus, it is intended that the present invention cover any modifications and variations of this invention.

Adaptation of the System of the Present Invention for Use with a Mechanical Ventilator Referring to FIG. 7A1, step "D," examples of specific main menu options for a mechanical ventilator will be described. If the care provider has selected review of the current protocol in Step 50, the interface 14 provides the care provider with a variety of information (FIG. 7A2). The care provider is told tidal volume (Step 51); the breath rate (Step 52); the high pressure setting (Step 53); the mode (Step 54); the peak flow (Step 55); the low pressure setting (Step 56); the PEEP level (Step 57); the elapsed time (Step 58); and the last alarm (Step 59). After providing this information to the care provider, the interface 14 in Step 60 returns to the main menu as FIG. 3.

With reference to FIG. 7A2, the edit mode will be described in detail. If the care provider has selected the edit mode in Step 61, the interface 14 permits the care provider to edit the current protocol. In this mode, some parameters may be maintained while others may be edited. The care provider is requested to enter the serial number of the mechanical ventilator (Step 62), the care provider identification number (Step 63), and the patient's identification number (Step 64). These numbers are for record keeping purposes, and are included in any report or file requested by the care provider. In Step 65 the care provider is told the current tidal volume. The care provider is then asked to enter a new rate, or press the # button on the keypad to accept the new rate (Step 66). Similar operations are performed on the breath rate, the high pressure setting, mode, current peak flow, low pressure setting, and PEEP level (Steps 67-78). After editing, the interface 14 transfers to the sub-menus of FIG. 7D (Circle G).

Figure 7B:
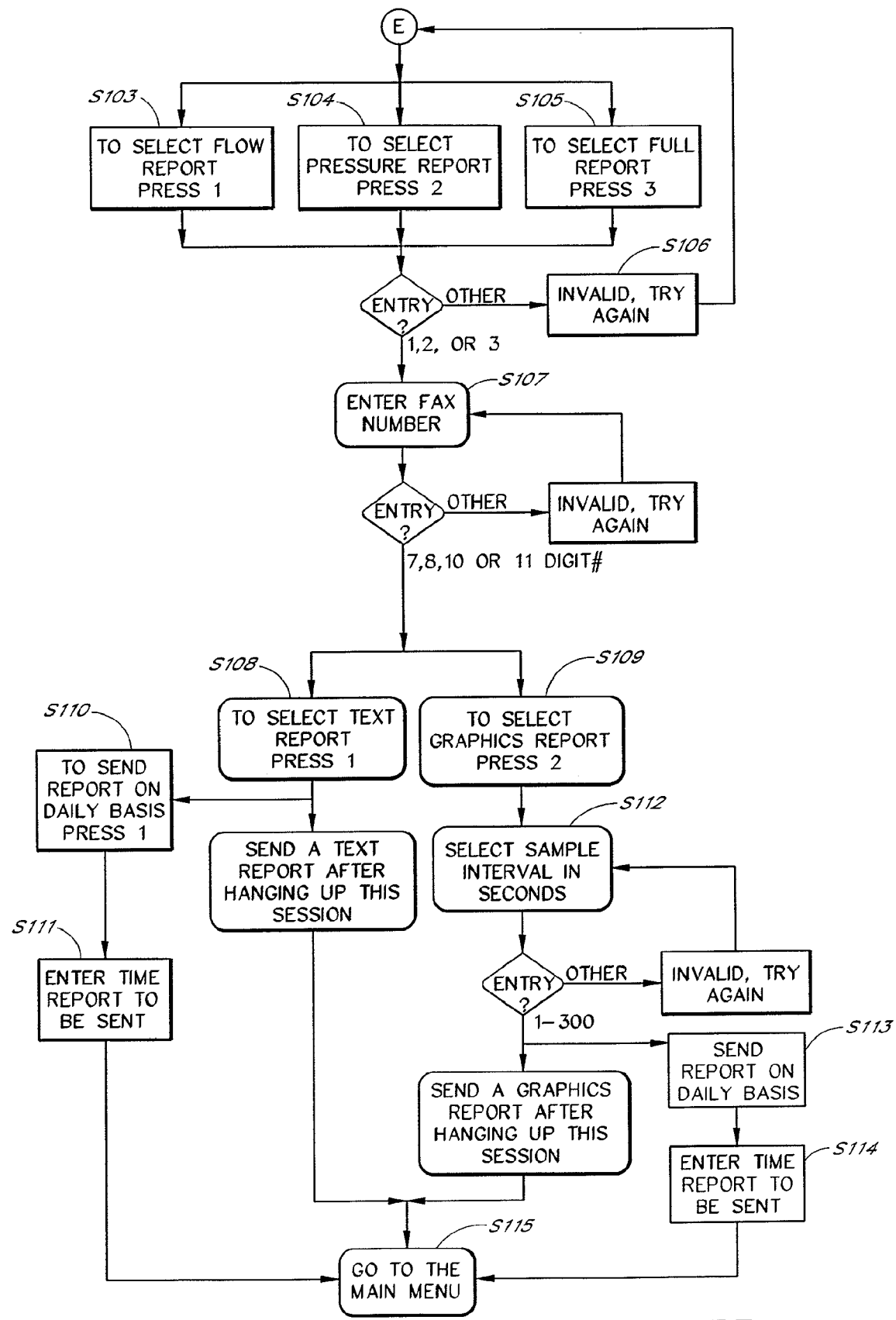
FIG. 7B is a flow diagram illustrating a fax report menu of the system as adapted to use with a mechanical ventilator.
Figure 7C:
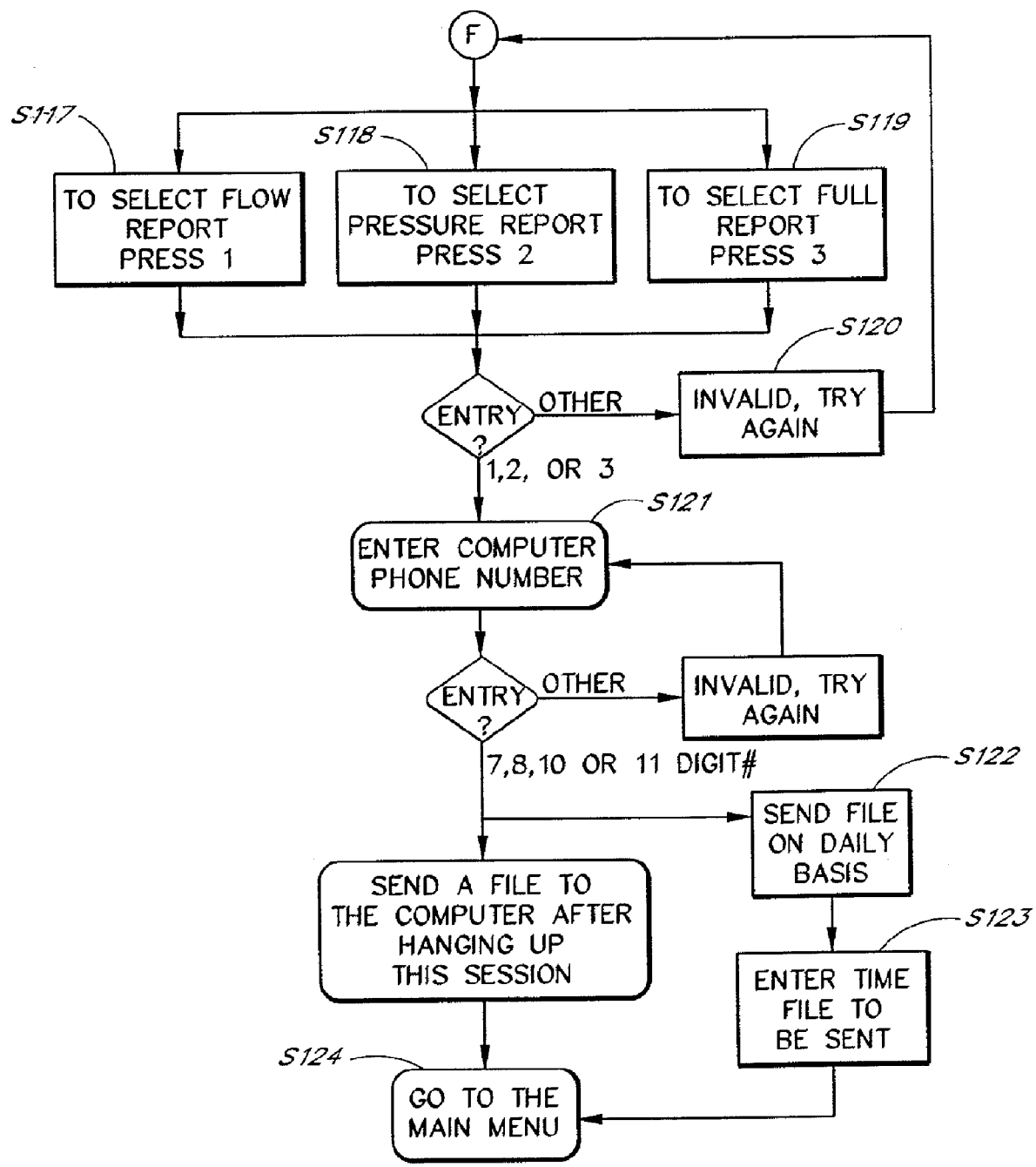
FIG. 7C is a flow diagram illustrating a send file menu of the system as adapted to use with a mechanical ventilator.
Figure 7D:
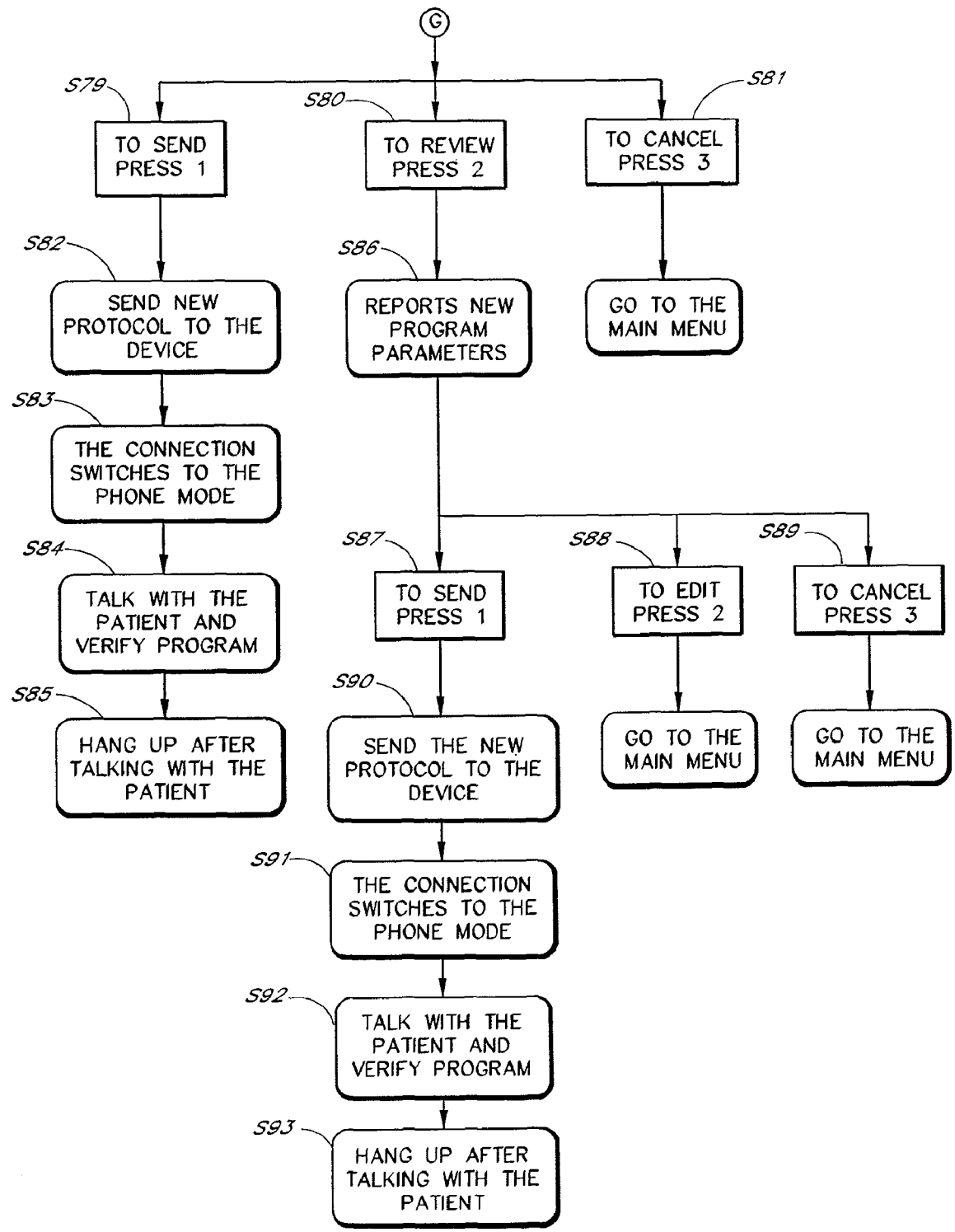
FIG. 7D is a flow diagram illustrating an edit protocol sub-menu of the system as adapted to use with a mechanical ventilator.

Referring now to FIG. 7D, the edit mode sub-menus provide the care provider with several options after editing the protocol. The first edit mode sub-menu allows the care provider to send (i.e., save) the edits to the ventilator by pressing a certain key on the keypad (Step 79), to review the edits by pressing a different key on the keypad (Step 80), and to cancel the edits by pressing still a different number on the keypad (Step 81). If the care provider selects sending the edits (Step 79), the new protocol is sent to the respirator (Step 82), and the care provider is told goodbye. The care provider is then transferred to patient conversation mode (Step 83), and the care provider is put in connection with the patient to verify the programming (Step 84). After verifying the programming changes with the patient, the care provider hangs up the remote telephone 48 (Step 85), and the programming session is completed.

If the care provider selects reviewing the edits (Step 80), the interface 14 reports the new parameters of the protocol to the care provider (Step 86). After reporting, the care provider is taken to the second edit mode sub-menu which permits the care provider to select: (1) send the edits (Step 87), (2) edit the edits (Step 88), or (3) cancel the edits (Step 89). If the care provider selects sending the amended protocol (Step 87), the new protocol is sent to the respirator (Step 90), and the care provider is told goodbye. The care provider is then transferred to patient conversation mode (Step 91), and the care provider is put in connection with the patient to verify the programming (Step 92). After verifying the programming changes with the patient, the care provider hangs up the remote telephone (Step 93) and the programming session is terminated.

If the care provider selects the create mode in Step 94 (see FIG. 7A1), the care provider is asked to program various parameters for the new protocol. As illustrated in FIG. 7A2, the care provider is asked to enter the tidal volume (Step 95) after which the entered tidal volume is read back, and the care provider is asked to press the # button to accept this rate. The care provider follows the same procedure for entering breath rate, high pressure setting, mode, peak flow, low pressure setting, and PEEP level (Steps 96-101), and then the same control menu as illustrated in FIG. 7D.

If the care provider selects the fax report mode in Step 102, the interface 14 generates a number of queries that are transmitted to the care provider and provide the care provider with a number of options. Referring now to FIG. 7B, Step 103, the care provider has the option of selecting a flow report, a pressure report (Step 104), or a full report (Step 105). If the care provider enters a number which is not an option (Step 106) the interface unit returns to Circle E. Next, the care provider is asked in Step 107 to enter the fax number of the location where the report is to be sent. In Step 108, the care provider may select a text report by pressing a certain button on the keypad or a graphics report by pressing a different button (Step 109). If the care provider selects the text report, in Step 108 the care provider may then select to have the text report sent to the fax number on a daily basis by pressing a button on the keypad (Step 110). If the care provider chooses to request that the medical device remote system send a daily report to the fax number, the care provider then enters the time via the touch-tone keypad that the report will be sent to the number (e.g., 1430 for 2:30 PM) (Step 111). If the care provider selects a graphics report (Step 109), the interface 14 asks the care provider to select a sample time interval (in seconds) from 1-300 seconds (Step 112). If the care provider chooses to request that the medical device remote system send a daily graphics report to the fax number (Step 113), the care provider then enters the time via the touch-tone keypad that the report will be sent to the number (e.g., 1430 for 2:30 PM) (Step 114). If the care provider chooses not to have a daily report, then the care provider will return to the main menu (Step 115) whereby the graphics report will be sent to the fax number after the session is completed.

If the care provider selects the send file mode in Step 116, the care provider is transferred to the send file menu (Circle F) in FIG. 7C. Steps 117-124 are similar to the steps above for faxing a report except that the computer phone number is entered (Step 121) instead of a fax number so that the report file is sent to a computer instead of a fax. The care provider also has the option of having the medical device remote system send the file to a remote computer on a daily basis (Steps 122-123).

Figure 8A:
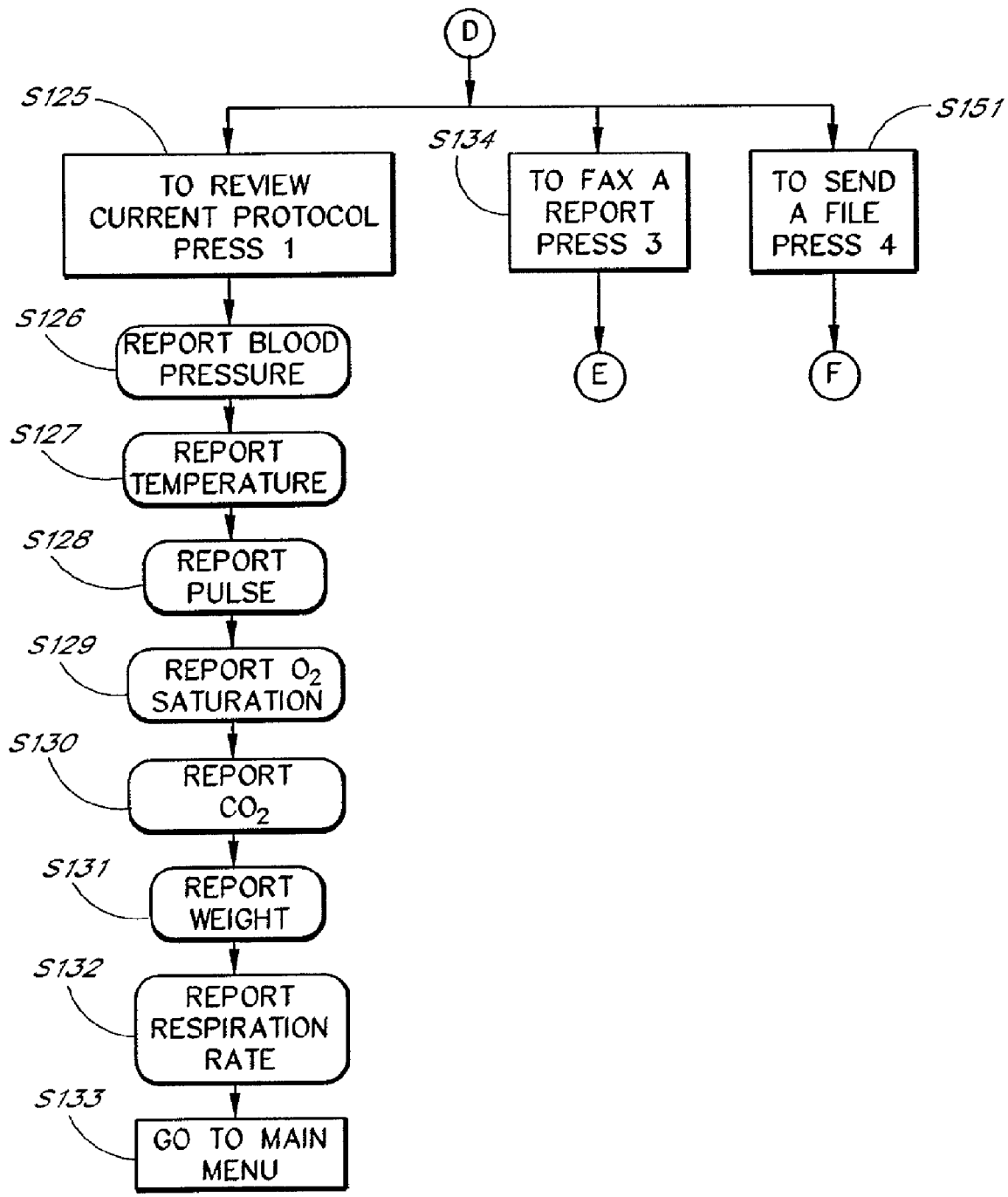
FIG. 8A is a flow diagram illustrating a portion of a main menu of the system illustrated in FIG. 3 as adapted to use with a vital signs monitor.

Adaptation of the System of the Present Invention For Use With a Vital Signs Monitor Referring to FIG. 8A, Circle D, examples of the specific main menu options when the medical device comprises a vital signs monitor will be described. Such a monitor generally obtains patient data such as blood pressure, temperature, pulse rate, 02 saturation, CO2 level, weight and/or respiration rate. If the care provider has selected review of the current protocol in Step 125, the interface 14 provides the care provider with a variety of information. The care provider is told the blood pressure (Step 126); the temperature (Step 127); the pulse (Step 128); the 02 saturation (Step 129); the carbon dioxide level (Step 130); the weight (Step 131); and the respiration rate (Step 132). After providing this information to the care provider, the interface 14 in Step 133 returns to the main menu.

Figure 8B:
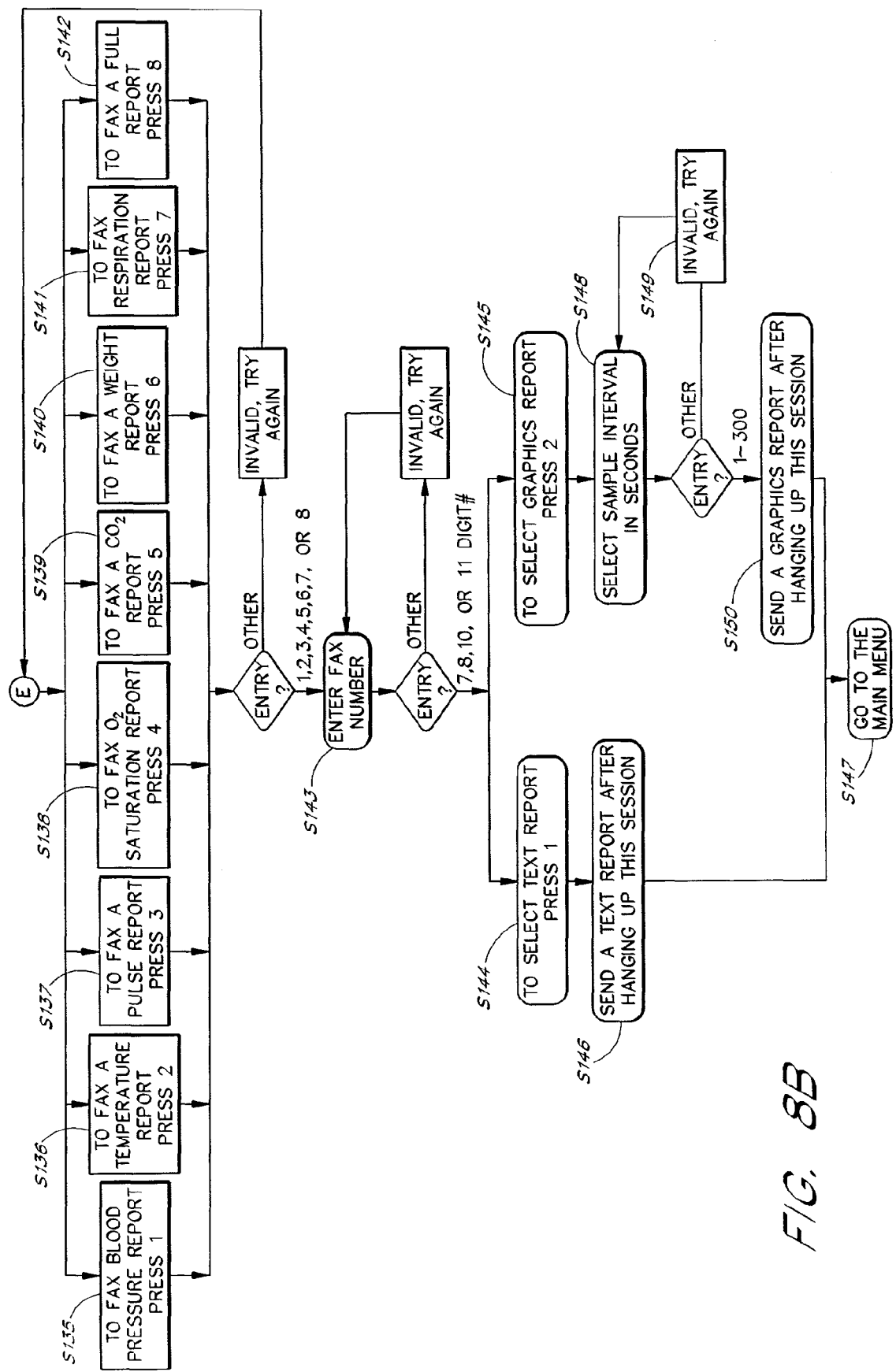
FIG. 8B is a flow diagram illustrating a fax report menu of the system as adapted to use with a vital signs monitor.

If the care provider selects the fax report mode in Step 134, the care provider is transferred to the fax report menu as illustrated in FIG. 8B. Upon accessing this menu, the interface 14 generates a number of voice queries that are transmitted to the care provider and provide the care provider with a number of options. The care provider has the option of selecting a: (1) blood pressure report, (2) temperature report, (3) pulse report, (4) 02 saturation report, (5) carbon dioxide report, (6) weight report; (7) respiration report, or (8) full report, by pressing 1-8, respectively on the touch-tone keypad (Steps 135-142). Next, the care provider is asked in Step 143 to enter the fax number of the location where the report is to be sent. In Step 144, the care provider may select a text report by pressing a certain button on the touch-tone keypad or a graphics report by pressing a different button (Step 145). If the care provider selects a text report, interface 14 tells the care provider to enter a certain number on the touch tone keypad to hang up and end the session (Step 146) whereby the text report will be sent to the fax number or enter a different number if the care provider wants to return to the main menu (Step 147) whereby the text report will be sent to the fax number after the session is completed. If the care provider selects a graphics report (Step 145), the interface 14 asks the care provider to select a sample time interval (in seconds) from 1-300 seconds (Step 148). If an invalid number is selected (Step 149), the interface 14 returns to Step 148. The care provider then enters a certain number on the touch tone keypad to hang up and end the session whereby the graphics report will be sent to the fax number (Step 150) or enter a different number (in this case the number "2") if the care provider wants to return to the main menu whereby the graphics report will be sent to the fax number after the session is completed (Step 147).

Alternatively, the device 10 may store a fax number and the device could be programmed to send faxes including desired information at specific times.

Figure 8C:
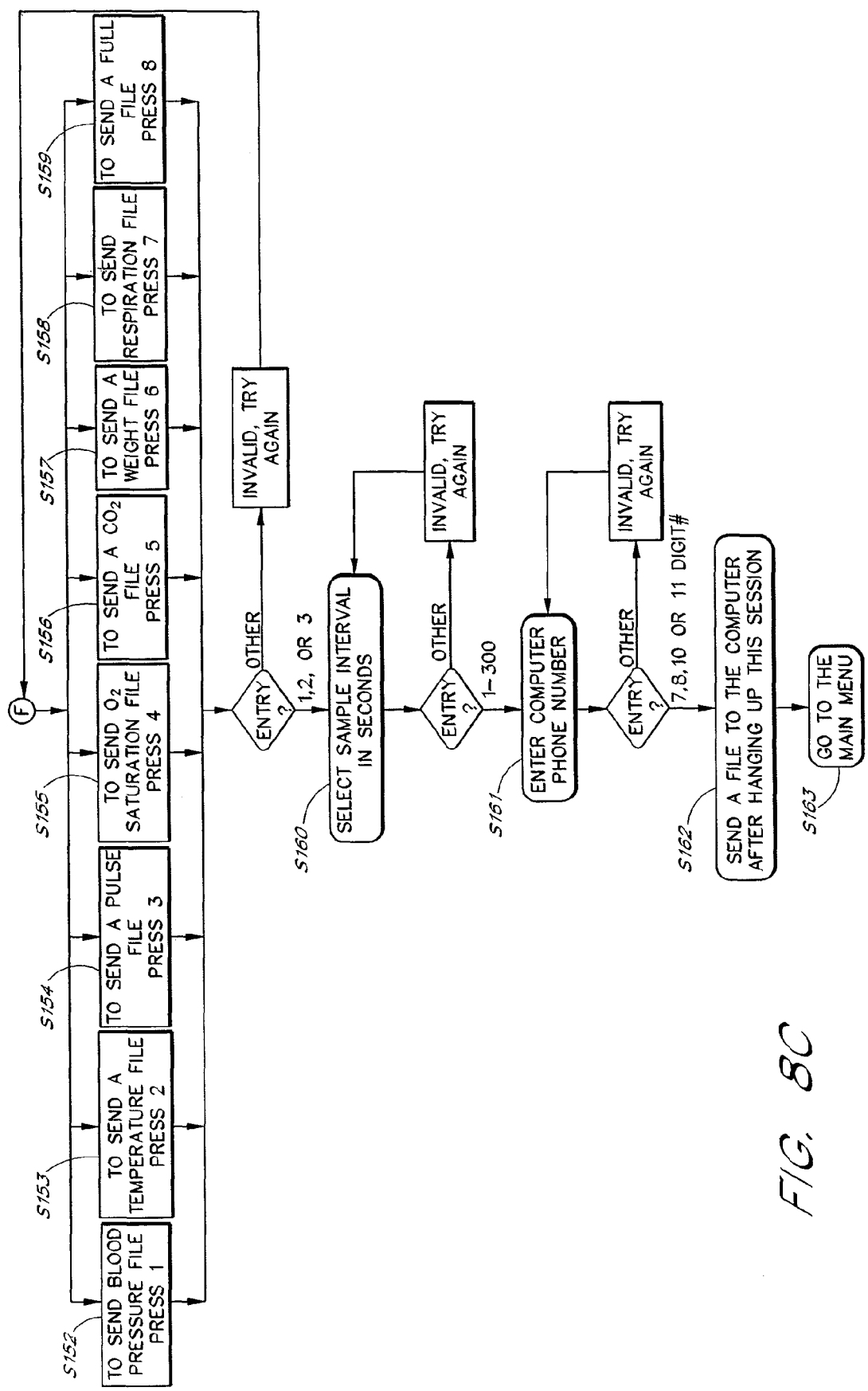
FIG. 8C is a flow diagram illustrating a send file menu of the system as adapted to use with a vital signs monitor.

If the care provider selects the send file mode in Step 151, the care provider is transferred to the send file menu (Circle F) illustrated in FIG. 8C. Steps 152-163 are similar to Steps 135-147 above except that the care provider must enter a sample time interval (Step 160) and the computer phone number is entered instead of a fax number (Step 161) so that the report file is sent to a computer instead of a fax. Further, the device 10 may be programmed to send e-mails via a communication network such as the Internet. In this feature of the invention, the device would be programmed to log onto the communication network, enter a password stored in memory and send an e-mail report.

In another aspect of the present invention, the device may be programmed to ask a patient questions regarding how they feel, how much pain they are experiencing, etc. The answers to these questions may be accessed by a care provider to assist the care provider in programming the protocol of the device as will be understood by those of skill in the art. For example, if a patient indicates that he or she is feeling good, the care provider may not edit the protocol. This feature of the invention permits the care provider to access more information and better treat the patient. A patient may input their data through the device 10 itself, through the local phone 48A or in other ways such as through a computer, etc. The patient could enter this data whenever the patient's condition changes or be prompted, i.e., by a telephone call or an alarm on the device 10, to enter the information at fixed intervals.

In accordance with the present invention, there is provided a medical system which permits the remote access and control of a medical device. The system is arranged to permit a caregiver to control the medical device from a remote phone, computer or other transceiver. The caregiver may obtain date from the medical device, such as in the form of a written report (such as by facsimile), by voice data, or by graphical or alphanumeric data provided to a computer (which may be presented as graphs or other data on a screen and/or stored in a computer memory). The caregiver may also program the medical device if the device stores a programmable protocol. In addition, the system is arranged to that an alarm signalled by the medical device is then triggered remotely as well.

Specific examples of the adaptation of the system of the invention to specific medical devices are described above. Those of skill in the art will appreciate the adaptation of the system to a wide variety of other medical devices.

Of course, the foregoing description is that of preferred embodiments of the invention, and various changes and modifications may be made without departing from the spirit and scope of the invention, as defined by the appended claims.

What is claimed is:

1. A method of providing healthcare to a patient from a remote location, comprising:
   initiating, using a telephone at a first location, a connection with a medical device system associated with a patient, said patient and said medical device system, with the exception of said telephone and a communication network connecting said telephone and said medical device system, being present at a second location remote from said first location;
   receiving a menu query in the form of a stored voice signal including a menu option for programming an operating protocol for a medical device connected to said patient;
   selecting said option for programming said operating protocol by transmitting over said network a touchtone signal generated by a touchtone keypad of said telephone;
   modifying at least one parameter of said operating protocol for said medical device by transmitting over said network a touchtone signal generated by said touchtone keypad;
   saving said modified operating protocol; and
   ending said connection with said medical device system.

2. The method of claim 1, additionally comprising the step of reviewing patient data stored in a memory of said medical device system by transmitting a touchtone signal from said telephone and receiving at said telephone a voice signal from said medical device system.

3. The method of claim 1, additionally comprising the step of initiating voice communication with said patient between a patient telephone at said second location and said telephone at said first location over said communication network without ending said connection over said communication network.

4. The medical device system of claim 1, wherein said manipulation of said programmable protocol and said review of said patient data may be accomplished using only the 0, 1, 2, 3, 4, 5, 6, 7, 8, 9, 0, star and pound keys of said touchtone keypad.

5. The method of claim 1, wherein said selecting step, said modifying step and said saving step may be accomplished using only the 0, 1, 2, 3, 4, 5, 6, 7, 8, 9, 0, star and pound keys of said touchtone keypad.

* * * * *